US006221602B1

(12) United States Patent
Barbera-Guillem et al.

(10) Patent No.: US 6,221,602 B1
(45) Date of Patent: *Apr. 24, 2001

(54) FUNCTIONALIZED NANOCRYSTALS AND THEIR USE IN LABELING FOR STRAND SYNTHESIS OR SEQUENCE DETERMINATION

(75) Inventors: Emilio Barbera-Guillem, Powell; M. Bud Nelson, Worthington; Stephanie L. Castro, Columbus, all of OH (US)

(73) Assignee: Bio-Pixels Ltd., Westerville, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/436,159

(22) Filed: Nov. 9, 1999

Related U.S. Application Data
(60) Provisional application No. 60/107,829, filed on Nov. 10, 1998, and provisional application No. 60/109,626, filed on Nov. 24, 1998.

(51) Int. Cl.[7] .............................. C12P 19/34; C12Q 1/68; G01N 33/533; G01N 21/64; G01N 3/30
(52) U.S. Cl. ........................ 435/6; 435/91.1; 436/546; 422/82.08; 356/317; 250/307; 250/459.1
(58) Field of Search ................................. 250/307, 459.1; 356/317; 422/82.08; 436/546; 435/6, 91.1

(56) References Cited

U.S. PATENT DOCUMENTS 4,496,675 * 1/1985 Hille et al. ............................ 524/77
4,535,130 * 8/1985 Favie et al. ......................... 525/327.3
5,945,504 * 8/1999 Amagi et al. ......................... 528/373
5,990,479 * 11/1999 Weiss et al. .......................... 250/307

OTHER PUBLICATIONS

Stratagene Catalog, p. 39, 1988.*
Jacoby, "Quantum dots meet biomolecules", C&EN, 1998, Sep. 28, p.8.
Emory et al., "Direct observation of size-dependent optical enhancement in single metal nanoparticles", 1998, J. Am. Chem. Soc., vol. 12: 8009–8010.
Chan and Nie, "Quantum dot bioconjugates for ultrasensitive nonisotopic detection", Science, vol. 281: 2016–2018.
Service, "Semiconductor beacons light up cell structures", Science, 1998, Sep. 25, vol. 281:1930–1931.
Bruchez et al., "Semiconductor nanocrystals as fluorescent biological labels", Science, 1998, Sep. 25, vol. 281:2013–2015.

* cited by examiner

Primary Examiner—Jeffrey Fredman
Assistant Examiner—Arun Kr. Chakrabarti
(74) Attorney, Agent, or Firm—M. Bud Nelson (57) ABSTRACT

Provided are compositions comprising functionalized nanocrystal-labeled nucleobases that are produced by operably linking a nucleobase to a functionalized nanocrystal via reactive functionalities. Also provided are kits comprising a plurality of species of functionalized nanocrystal-labeled nucleobases. The functionalized nanocrystal-labeled nucleobases may be added to a strand synthesis reaction under suitable conditions to be incorporated into one or more strands synthesized in the reaction.

22 Claims, 3 Drawing Sheets

Binding of amino-functionalized QD to maleimide

1. Organic soluble maleimides: stir QD with maleimide in $CHCl_3$ for 2 - 6 hours.

FUNCTIONALIZED NANOCRYSTALS AND THEIR USE IN LABELING FOR STRAND SYNTHESIS OR SEQUENCE DETERMINATION

This is a nonprovisional patent application based on earlier, co-pending provisional patent applications Serial Nos. 60/107,829, filed Nov. 10, 1998 and 60/109,626, filed Nov. 24, 1998 which are herein substantially incorporated by reference.

FIELD OF INVENTION

This invention relates generally to novel compositions comprising functionalized nanocrystals and nucleobases. More particularly, the present invention relates to the use of water-soluble nanocrystals to couple nucleobases, via reactive functionalities, in forming fluorescent-labeled nucleobases that can provide detectable signals for synthesized molecules containing the fluorescent-labeled nucleobases.

BACKGROUND OF THE INVENTION

DNA sequencing continues to be an important analytical tool for providing information relevant to laboratory research, biotechnology, clinical medicine, and drug discovery. In one method, the Maxam-Gilbert chemical degradation method, the DNA molecule to be sequenced is labeled at one end with a radioisotope, and then apportioned to four different reactions which together, are specific for all four bases. In each reaction, the DNA is cleaved at a specific nucleotide base (either guanine (G), cytosine (C), thymine (T), or adenine (A)). The four different sets of fragments are then electrophoresed to separate the fragments into bands based on their length, thus identifying the 3'-terminii positions defined by the cleavage of the given nucleotide base. In another method, the Sanger dideoxy chain termination method, the DNA sequence of a single-stranded template DNA is determined by using the template to synthesize multiple copies of the complementary strand. A primer is used to anneal to the template and to provide an initiation point from which synthesis proceeds. Typically, the annealed primer-template is added to four reactions, each of which is combined with four deoxynucleotide triphosphates ("dNTPs", e.g., dATP, dTTP, dCTP, dGTP), a DNA polymerase enzyme, and a single dideoxynucleotide triphosphate ("ddNTP"). The reaction conditions are designed so that the ddNTP competes with the dNTPs for incorporation into the synthesized strand; that the incorporation of the ddNTP into the strand prevents further extension; that different size strands are synthesized; that the synthesized strands may be separated into discrete band by electrophoresis; and that the sequence can be determined from the pattern of bands because each band corresponds colinearly to a specific nucleotide.

Typically, radioisotopes have been, and continue to be, used to label nucleotides to visualize the bands resulting from electrophoresis. However, there are several disadvantages inherent to using a radioisotope to label the nucleotides for a sequencing reaction, including problems associated with storage, use, and disposal of radioisotopes. Handling and disposing of radioactive gels and radioactive wastes are problematic as to logistics, and also involves issues related to health and safety. Use of fluorescent labels has become more commonplace in sequencing reactions. Many current automated DNA sequencing methods utilize fluorescence detection of labeled synthesized DNA strands. One method of fluorescence labeling is to use a single fluorophore in the four sets of reactions to generate the synthesized strands which are then loaded into adjacent lanes and separated by electrophoresis. Use of a single fluorophore is disadvantageous because (a) automated scanning of four lanes can be difficult due to lane-to-lane variations in the migration velocity of electrophoresing synthesized strands; and (b) four lanes are needed, as each of the four reactions need be loaded into a separate lane, thereby reducing throughput.

There exists fluorescence-based DNA sequencing systems using fluorophores. U.S. Pat. No. 5,723,298 describes a method using two cycles of primer extensions, wherein the primer extension product is labeled by incorporating a fluorescent fluorophor-labeled dNTP. This technology is representative of the single-label/four-lane system. U.S. Pat. No. 5,436,130 describes the use of two different fluorescent dyes to label nucleotides used as terminators in strand synthesis. A system utilizing multi-color detection and different fluorescent dyes would be desirable. Such systems have been described previously, and have encountered various problems in application. For example, in one system the primers are labeled with four different dyes (Smith et al., 1985, Nucleic Acids Res. 13:23999–2412). However, use of the four dyes utilized appears to cause significant perturbations in electrophoretic mobilities, thereby making sequence interpretations difficult. Properties that may effect such perturbations include the difference in molecular size, charge, and shape of the dyes utilized.

Other systems have been proposed, wherein up to four different fluorescent dyes are used in a sequencing method, and wherein each dye has a different excitation wavelength and a different emission wavelength. However, one would expect to have to use more than one excitation light source to provide the necessary excitation wavelengths required (see, e.g., U.S. Pat. Nos. 5,675,155, and 5,650,277). Additionally, a large wavelength range (e.g., 100 nm between different excitation wavelength spectrum) for excitation of a combination of fluorescent dyes used in the same system makes it difficult to excite the combination with a single monochromatic light source. Further, a large dynamic range in the detectable signal intensities emitted by four different fluorescent dyes presents difficulties in the detection process. However, use of fluorescent dyes having closely spaced absorption (excitation) and corresponding emission wavelengths could present difficulties in distinguishing between the different emission spectra in order to identify the individual labeled synthesized strands.

Thus, there continues to be a need for a class of fluorescent molecules which can be used in combinations in preparing labeled nucleobases for nucleic acid molecule strand synthesis, and particularly for automated DNA sequencing. For example, in nucleic acid molecule synthesis and amplification, there remains a need for a nonisotopic detection system which can be used in the detection of nucleic acid molecules; and which utilizes a class of molecules that may be excited with a single excitation light source resulting in detectable fluorescence emissions of high quantum yield and with spectrally resolvable fluorescence peaks, thereby allowing simultaneous detection of several colors by an appropriate detection system.

SUMMARY OF THE INVENTION

It is a primary object of the present invention to provide compositions for an improved method of detecting strand synthesis and/or sequencing.

It is another object of this invention to provide compositions comprising a class of functionalized nanocrystals which can be used in combination as labels in a reaction comprising strand synthesis, sequencing, or a combination thereof.

It is a further object of this invention to provide a method of sequencing, wherein the synthesized strands are labeled using different functionalized nanocrystals according to the present invention, and wherein the spectrally resolvable emission spectra of the functionalized nanocrystals is employed to detect the strands or sequence.

The foregoing and other objects of the present invention are achieved by providing compositions according to the present invention, wherein the compositions comprise functionalized nanocrystals that can be operably linked to nucleobases, wherein a resultant functionalized nanocrystal-labeled nucleobase can be incorporated into a strand such as during strand synthesis. According to the present invention, provided is a single set comprised of at least four species of functionalized nanocrystal labels which are (a) efficiently excited by a single light source; (b) have closely spaced emission spectra that are spectrally resolvable by peak emission wavelengths; (c) are substantially similar as to general size, shape, and charge; (d) have emissions of relatively high quantum efficiency; (e) are small enough in size so that when used to label a nucleobase, may minimize possible steric hinderance as related to incorporation of the labeled nucleobase and/or the progression of strand synthesis. For example, in one method of using the functionalized nanocrystals according to the present invention as labels, it would be possible to sequence a DNA molecule by carrying out a single reaction in which at least four species of functionalized nanocrystals having discrete fluorescence emission spectra are used to differentially label different nucleobases incorporated into a synthesized strand, resolving the resultant differentially labeled synthesized strands (e.g., such as by size, length, or time), exciting the synthesized strands with an excitation light source, and then scanning for detection by a fluorimeter that is capable of spectrally resolving the discrete fluorescence spectra of the excited functionalized nanocrystal labels.

The above and other objects, features, and advantages of the present invention will be apparent in the following Detailed Description of the Invention when read in conjunction with the accompanying drawings.

DETAILED DESCRIPTION OF THE INVENTION

Definitions

By the term "nucleic acid amplification" is meant, for purposes of the specification and claims to refer to a process by which a nucleic acid sequence may be amplified in number/quantity. There are several means, and conditions for achieving those means, known to those skilled in the art for enzymatically amplifying nucleic acid sequences including polymerase chain reaction, ligase chain reaction, and nucleic acid sequence-based amplification.

By the term "operably link" is meant, for purposes of the specification and claims to refer to chemical fusion or bond or an association of sufficient stability to withstand conditions encountered in the method of strand synthesis utilized, between a combination of different molecules such as, but not limited to: between a linker and a functionalized nanocrystal; between a linker and a nucleobase; between a functionalized nanocrystal and a nucleobase; between the quantum dot and a capping compound; between a capping compound and a diaminocarboxylic acid; between a diaminocarboxylic acid and a diaminocarboxylic acid; between a diaminocarboxylic acid and a linker; between a diaminocarboxylic acid and an amino acid; between an amino acid and a nucleobase; between a diaminocarboxylic acid and a nucleobase; and a combination thereof. "Operably link" also preferably means, for purposes of the specification and claims, that a functionalized nanocrystal-labeled nucleobase, is performed in such a way that the resultant labeled nucleobase can be readily incorporated into an elongating strand by a polymerase during strand synthesis. As known to those skilled in the art, and as will be more apparent by the following embodiments, there are several methods and compositions in which two or more molecules may be operably linked utilizing reactive functionalities. Reactive functionalities comprise bifunctional reagents/linker molecules, free chemical groups (e.g., thiol, or carboxyl, hydroxyl, amino, amine, sulfo, etc.), reactive chemical groups (reactive with free chemical groups), and a combination thereof.

By the term "linker" is meant, for purposes of the specification and claims to refer to a compound or moeity that acts as a molecular bridge to operably link two different molecules, wherein one portion of the linker binds to a functionalized nanocrystal according to the present invention, and wherein another portion of the linker binds to a nucleobase. The two different molecules may be linked to the linker in a step-wise manner. There is no particular size or content limitations for the linker so long as it can fulfill its purpose as a molecular bridge suitable for use in strand synthesis. Linkers are known to those skilled in the art to include, but are not limited to, chemical chains, chemical compounds (e.g., reagents), and the like. The linkers may include, but are not limited to, homobifunctional linkers and heterobifunctional linkers. Heterobifunctional linkers, well known to those skilled in the art, contain one end having a first reactive functionality to specifically link a first molecule, and an opposite end having a second reactive functionality to specifically link to a second molecule. The reactive functionalities of the linker are selected from the group consisting of amino-reactive groups and thiol-reactive groups. That is, the linker should be able to function to operably link by interacting with either a free thiol group or a free amino group present on either or both of the functionalized nanocrystal and the nucleobase to be linked. Depending on such factors as the molecules to be linked, and the conditions in which the method of strand synthesis is performed, the linker may vary in length and composition for optimizing such properties as stability, resistance to certain chemical and/or temperature parameters, and of sufficient stereo-selectivity or size to operably link the label to the nucleobase such that the resultant labeled nucleobase may be stably incorporated into a synthesized strand during strand synthesis. For example, the linker should not significantly interfere with the ability of the functionalized nanocrystal-labeled nucleobase (e.g., DNTP) from binding to or being incorporated by DNA polymerases into a synthesized strand. Such linkers can be employed using standard chemical techniques. Such linkers are known to those skilled in the art to include, but are not limited to, amine linkers for attaching labels to nucleobases (see, e.g., U.S. Pat. No. 5,151,507); a linker preferably contain a primary or secondary amine for operably linking a label to a nucleobase; and a rigid hydrocarbon arm added to a nucleotide base (see, e.g., *Science* 282:1020–21, 1998).

By the term "strand synthesis" is meant for purposes of the specification and claims to refer to the production of one more strands, or portions thereof, such as through enzymatic copying by an enzyme which replicates nucleic acids in a template-directed manner. There is no particular size, length or content limitations for the strand. Thus, "strand synthesis" encompasses processes including, but not limited to, nucleic acid amplification, DNA sequencing, fill-in reactions, reverse transcription, in vitro mutagenesis, cycled chain termination sequence reactions, cycled primer extension reactions, random primer extension reactions, nick translations, primer elongation, methods for determining the presence and quantifying the number of di- and trinucleotide repeats (see, e.g., U.S. Pat. No. 5,650,277), and DNA typing with short tandem repeat polymorphisms (see, e.g., U.S. Pat. No. 5,364,759). The nucleic acid composition of the strand synthesized may be selected from molecules which include nucleobases; and more preferably, ribonucleotides (RNA), or deoxyribonucleotides (DNA).

By the term "spectrally resolvable" is meant when used in conjunction with a set comprised of species of the class of functionalized nanocrystals according to the present invention, and for purposes of the specification and claims, that the peak flourescence emission for each of the functionalized nanocrystals in the set are sufficiently distinct (e.g., sufficiently discrete) so as to be distinguishable (and hence can be utilized to identify a nucleobase operably linked thereto) on the basis of the fluorescent signal generated by the respective, excited functionalized nanocrystals by standard photodetection systems known in the art (e.g., employing a system of one or more photodetectors, filters, and the like).

By the term "DNA sequencing" is meant, for purposes of the specification and claims to refer to a process by which a nucleic acid sequence is determined. There are several means, and conditions for achieving those means, known to those skilled in the art for DNA sequencing including, but not limited to, the Maxam-Gilbert technique, Sanger dideoxy chain termination method, capillary sequencing techniques (see, e.g., U.S. Pat. No. 5,675,155), DNA sequencing with one of several available polymerases (see, e.g., U.S. Pat. Nos. 5,502,773, 5,516,633, 5,374,527, 4,994,372), cycled primer extension coupled with cycled chain termination reaction (see, e.g., U.S. Pat. No. 5,723,298), automated DNA sequencing methods, and mixed-mode fluorescent DNA sequencing (see, e.g., De Bellis et al, 1994, *BioTechniques* 16:1112–1115).

By the term "nucleobase" is meant, for purposes of the specification and claims to refer to a nucleic acid moiety including, but not limited to: nucleosides (including derivatives, or functional equivalents thereof, and synthetic or modified nucleosides, and particularly, a nucleoside comprising a reactive functionality (e.g., free amino group or carboxyl group); nucleotides (including dNTPs, ddNTPs, derivatives or functional equivalents thereof, and particularly, a nucleotide comprising a reactive functionality (e.g., free amino group or carboxyl group); acyclonucleoside triphosphates (see, e.g., U.S. Pat. No. 5,558,991); 3'(2')-amino-modified nucleosides, 3'(2')-amino-modified nucleotides, 3'(2')-thiol-modified nucleosides, 3'(2')-thiol-modified nucleotides (see, e.g., U.S. Pat. No. 5,679,785); alkynylamino-nucleotides (see, e.g., as a chain terminator, U.S. Pat. No. 5,151,507); and nucleoside thiotriphosphates (see, e.g., U.S. Pat. No. 5,187,085).

By the term "diaminocarboxylic acid" is meant, for purposes of the specification and claims to refer to an amino acid that has two free amine groups. The amino acid may be a naturally occurring amino acid, a synthetic amino acid, a modified amino acid, an amino acid derivative, an amino acid precursor (e.g., citrulline and ornithine are intermediates in the synthesis of arginine), or a combination thereof. In a preferred embodiment, the diaminocarboxylic acid contains neutral (uncharged) polar functional groups which can hydrogen bond with water, thereby making the diaminocarboxylic acid (and the quantum dot to which it is made a part of) relatively more soluble in aqueous solutions containing water than those with nonpolar functional groups. Additionally, the diaminocarboxylic acid imparts one or more functional advantages to the water-soluble nanocrystal of which it is a part, as will be more apparent from the following embodiments Exemplary diaminocarboxylic acids include, but are not limited to, lysine, asparagine, glutamine, arginine, citrulline, ornithine, 5-hydroxylysine, djenkolic acid, β-cyanoalanine, a synthetic diaminocarboxylic acid (e.g., such as 3,4-diaminobenzoic acid, 2,3-diaminopropionic acid, 2,4-diaminobutyric acid, 2,5-diaminopentanoic acid, 2,6-diaminopimelic acid), and a combination thereof. A diaminocarboxylic acid of the aforementioned diaminocarboxylic acids may be used in a preferred embodiment, and a preferred diaminocarboxylic acid may be used separately in the method according to the present invention to the exclusion of diaminocarboxylic acids other than the preferred diaminocarboxylic acid.

By the term "amino acid" is meant, for purposes of the specification and claims to refer to a molecule that has at least one free amine group and at least one free carboxyl group. The amino acid may have more than one free amine group, or more than one free carboxyl group, or may further comprise one or more free chemical reactive groups other than an amine or a carboxyl group (e.g., a hydroxyl, a sulfhydryl, etc.). The amino acid may be a naturally occurring amino acid, a synthetic amino acid, a modified amino acid, an amino acid derivative, and an amino acid precursor. The amino acid may further be selected from the group consisting of a monoaminocarboxylic acid, and a diaminocarboxylic acid. In a preferred embodiment, the monoaminocarboxylic acid contains one or more neutral (uncharged) polar functional groups which can hydrogen bond with water, thereby making the monoaminocarboxylic acid (and the quantum dot to which it is made a part of) relatively more soluble in aqueous solutions containing water than those with non-polar functional groups. Exemplary monoaminocarboxylic acids include, but are not limited to, glycine, serine, threonine, cysteine, β-alanine, homoserine, γ-aminobutyric acid, and a combination thereof. An amino γ-aminobutyric acid, and a combination thereof. An amino acid of the aforementioned amino acids may be used in a preferred embodiment, and a preferred amino acid may be used separately in the method according to the present invention to the exclusion of amino acids other than the preferred amino acid.

By the term "capping compound" is meant, for purposes of the specification and claims to refer to a compound having the formula HS(CH$_2$)$_n$X, wherein X is a carboxylate (carboxylic moiety); or the formula HS(CH$_2$)$_n$YX, wherein X is a carboxylate and Y is an amine; as will be more apparent from the following descriptions. "n" is a number in the range of from 1 to about 20, and preferably greater than 4. The thiol group of the capping compound forms Cd (or Zn)-S bonds (depending on whether the shell is Cd or Zn), creating a layer which is not easily displaced in solution. Additionally, the carboxylic acid moiety and/or the amine of the capping compound imparts some water solubility to the capped quantum dots. Exemplary capping compounds include, but are not limited to, mercaptocarboxylic acid, or mercapto-functionalized amines (e.g., aminoethanethiol-HCl, homocysteine, or 1-amino-2-methyl-2-propanethiol-HCl), or a combination thereof. A capping compound of the aforementioned capping compounds may be used in a preferred embodiment, and a preferred capping compound may be used separately in the method according to the present invention to the exclusion of capping compounds other than the preferred capping compound.

By the term "functionalized nanocrystals" is meant, for purposes of the specification and claims to refer to water-soluble nanocrystals comprised of (in order from inner core to outward coatings or layers): a core of CdX wherein X is Se or Te or S; passivated with a shell preferably comprised of YZ wherein Y is Cd or Zn, and Z is S, or Se; coated with a capping compound; and coated with least one additional coating that (a) enhances stability and/or solubility in an aqueous environment; and (b) provides one or more reactive functionalities that may be used to operably link the functionalized nanocrystal to a nucleobase, or to a linker (one or more linker molecules) which may then be used to operably link the functionalized nanocrystal to a nucleobase. Thus, a functionalized nanocrystal may further comprise a nucleobase operably linked thereto. In a preferred embodiment, the at least one additional coat comprises amino acid, wherein each coating of amino acid contains neutral (uncharged) polar functional groups which can hydrogen bond with water, and comprises one or more types of free chemical reactive groups. In a more preferred embodiment, the at least one layer of amino acid that functionalizes the nanocrystal is comprised of a coating of diaminocarboxylic acid. A preferred functionalized nanocrystal may be produced, and used in the method and system according to present invention, to the exclusion of functionalized nanocrystals other than the preferred functionalized nanocrystals.

The present invention relates to compositions and methods for base sequencing of DNA and RNA which employs a class of functionalized nanocrystals for labeling nucleobases incorporated into a strand synthesized by enzymatic copying of a template by an enzyme which replicates nucleic acids in a template-directed manner. These nanocrystals are different in structural and functional properties when compared to fluorescent dyes which have been used and described previously as labels in nucleic acid sequencing. There are several ways in which the functionalized nanocrystals may be utilized to label nucleobases, depending upon the type of sequencing reaction used. For example, the functionalized nanocrystal may be operably linked to a nucleobase either prior to strand synthesis (e.g., for standard Sanger dideoxy chain termination method), post-strand synthesis but pre-cleavage (e.g., wherein the synthesized strand is immobilized), or post-strand synthesis but post-cleavage (e.g., wherein the synthesized strand is immobilized). In one preferred embodiment, of the four bases found in the synthesized strand (e.g., for DNA or for RNA), nucleobases corresponding to more than one of the four base types is operably linked to functionalized nanocrystals. For example, in a method of using the functionalized nanocrystals according to the present invention to sequence a DNA molecule, a single reaction is carried out in which four species of functionalized nanocrystals having different and spectrally resolvable fluorescence emission spectra are used to differentially label four different dideoxynucleotides, the resultant differentially labeled synthesized strands are resolved (e.g., by length), and then scanned by a fluorimeter that is capable of spectrally resolving the functionalized nanocrystal-labeled nucleobases by their difference in fluorescence emission. In a preferred embodiment of the method, a plurality (e.g., between 2 and 10 or more) species of functionalized nanocrystals may be used to differentially label different types of nucleobases. Preferably, each nucleobase that is operably linked to a functionalized nanocrystal is modified so that it has a reactive functionality comprising either an amino group or a thiol group. Preferably, each functionalized nanocrystal has a reactive functionality comprising either an amino group or a thiol group or a thiol reactive group or an amino reactive group that is utilized for operably linking to a nucleobase. As described herein in more detail, the functionalized nanocrystal may be directly operably linked to a nucleobase, or a linker may be used to operably link the functionalized nanocrystal to a nucleobase.

The compositions according to the present invention comprise quantum dots which are functionalized (a) to be water-soluble, and (b) to further comprise a nucleobase which is operably linked thereto. Desirable features of the basic quantum dots themselves include that the class of quantum dots can be excited with a single excitation light source resulting in a detectable fluorescence emission of high quantum yield (e.g., a single quantum dot having at a fluorescence intensity that may be a log or more greater than that a molecule of a conventional fluorescent dye) and with a discrete fluorescence peak. The quantum dots typically should have a substantially uniform size of less than 200 Angstroms, and preferably have a substantially uniform size in the range of sizes of from about 1 nm to about 5 nm, or less than 1 nm.

In that regard, quantum dots are preferably comprised of a core of CdX wherein X is Se or Te or S. Such quantum dots are well known in the art. CdX quantum dots can be passivated with an overlayering ("shell") uniformly deposited thereon. A preferred passivating shell is comprised of YZ wherein Y is Cd or Zn, and Z is S, or Se. Quantum dots having a CdX core and a YZ shell have also been generally described in the art. However, a feature of the quantum dots used to operably link to a nucleobase is that the quantum dots have been functionalized to be water-soluble nanocrystals. "Water-soluble" is used herein to mean that the nanocrystals are sufficiently soluble or suspendable in a aqueous-based solution including, but not limited to, water, water-based solutions, buffer solutions, that are used in one or more processes such as strand synthesis or sequence determination, as known by those skilled in the art.

Typically, CdX core/YZ shell quantum dots are overcoated with trialkylphosphine oxide, with the alkyl groups most commonly used being butyl and octyl. One method to make the CdX core/YZ shell quantum dots water-soluble is to exchange this overcoating layer with one which will make the quantum dots water-soluble. For example, a mercaptocarboxylic acid is used to exchange with the trialkylphosphine oxide. Exchange of the capping group is accomplished by treating the water-insoluble quantum dots with a large excess of mercaptocarboxylic acid, either neat (e.g., at 60° C.) or in CHCl$_3$ solution (Chen and Nie, 1998, *Science*

281:2016–2018), followed by extraction into water. The mercaptocarboxylic acid coating imparts some water solubility to the quantum dots, whereas quantum dots capped with trialkylphosphine oxide are soluble only in organic, non-polar (or weakly polar) solvents. Another method to make the CdX core/YZ shell quantum dots water-soluble is by the formation of a layer of silica around the dots (Bruchez et al., 1998, *Science* 281:2013–2015). An extensively polymerized polysilane shell imparts water solubility to nanocrystalline materials, as well as allowing further chemical modifications of the silica surface. However, depending on the nature of the coating group, quantum dots which have been reported as water-soluble may have limited stability in an aqueous solution, particularly when exposed to air (oxygen) and/or light. More particularly, oxygen and light can cause the molecules comprising the coating to become oxidized, thereby forming disulfides which destabilize the attachment of the coating molecules to the shell. Thus, oxidation may cause the coating molecules to migrate away from the surface of the quantum dots, thereby exposing the surface of the quantum dots in resulting in "destabilized quantum dots". Destabilized quantum dots form aggregates when they interact together, and the formation of such aggregates eventually leads to irreversible flocculation of the quantum dots. Additionally, carboxylate groups can cause non-specific binding, particularly to one or more molecules in a sample other than the target molecule, which is not desirable in a detection assay. Described herein are quantum dots consisting essentially of a core of CdX wherein X is Se or Te or S; the core is then passivated with a shell preferably comprised of YZ wherein Y is Cd or Zn, and Z is S, or Se; and the shell is overlayed with a capping compound. However, it has been discovered that such quantum dots have disadvantages, as will be more apparent from the following descriptions (see also, FIGS. 2A and 2B). Hence, in a preferred embodiment of the present invention, provided are functionalized nanocrystals which maybe used to operably link to nucleobases, and assay kits therefor.

EXAMPLE 1

In this embodiment is illustrated the production of exemplary, basic quantum dots appropriate for functionalization according to the present invention. The quantum dots comprise a CdSe core, and a ZnS shell, "(CdSe)ZnS", and a layer of capping compound. TOPO capped CdSe were produced by placing TOPO (5 g) in a vessel, and dried at 150° C. for 1 hour under vacuum. The vessel was then backfilled with argon and heated to 300° C. In a controlled environment, $CdMe_2$ (7.2 µl, 0.1 mmol) and 1 M trioctylphosphine-Se solution (90 µl, 0.09 mmol) and trioctylphosphine (5 ml) were mixed, and then placed into an injector. This mixture was added to the TOPO in a reaction vessel, previously removed from the heat, in a single continuous injection with vigorous stirring, thereby resulting in the temperature decreasing to about 180° C. The reaction vessel was then subjected to heat to raise the temperature 5° C. every 10 minutes. Aliquots may be removed from the reaction vessel at various time intervals (5 to 10 minutes) to monitor the increase in size of quantum dots over time, by the observation of the absorption spectra. The temperature may be changed, or the reaction halted, upon reaching quantum dots of the desired characteristics. For example, the reaction vessel was cooled to about 60° C., 40 ml of methanol was added to cause the quantum dots to flocculate. After centrifugation, a brightly colored liquid layer of quantum dots dissolved in trioctylphosphine remained. The methanol/TOPO layer was decanted off, and pyridine (10 ml) was added to the solution of quantum dots and allowed to stand for at least one hour. The quantum dots were then precipitated as a powder by addition of hexanes, and separated by centrifugation. The powder was washed once more with hexanes, then dissolved in 30 ml pyridine, and centrifuged to remove any reaction byproducts.

To prepare (CdSe)ZnS quantum dots, the pyridine solution (30 ml) was placed in a reaction vessel, rigorously degassed with an inert gas (e.g., argon), and refluxed for one hour before adjusting the temperature to approximately 100° C. Equimolar amounts of diethyl zinc (zinc source) and hexamethyldisilathiane (sulfide source) were dissolved in trioctylphosphine (2–4 ml) in a controlled environment (glove box) and loaded into an injector. A reaction vessel containing the CdSe dots dispersed in pyridine was heated under an atmosphere of argon, and the Zn and S were added dropwise, via the injector, with vigorous stirring of the mixture for 5–10 minutes. The mixture was left stirring for several hours. After cooling, the pyridine solution was centrifuged to remove any insoluble material. The passivated quantum dots were stored in this solution to ensure that the surface of the quantum dots remained passivated with pyridine.

To cap the quantum dots, the pyridine overcoating of the (CdX) core/YZ shell quantum dots were exchanged with a capping compound which contributes to the water-solubility of the capped quantum dots. For example, a capping compound comprising mercaptocarboxylic acid may be used to exchange with the pyridine overcoat. Exchange of the coating group is accomplished by treating the water-insoluble, pyridine-capped quantum dots with a large excess of neat mercaptocarboxylic acid. To accomplish this, the pyridine-capped (CdSe)ZnS quantum dots were precipitated with hexanes, and then isolated by centrifugation. The residue was dissolved in neat mercaptoacetic acid, with a few drops of pyridine added, if necessary, to form a transparent solution. The solution is allowed to stand at room temperature for at least six hours. Longer incubation times lead to increased substitution by the thiol. overnight incubations are ideal. Chloroform is added to precipitate the quantum dots and wash away excess thiol. The quantum dots were isolated by centrifugation, washed once more with chloroform, and then washed with hexanes. The residue was briefly dried with a stream of argon. The resultant quantum dots were resuspended in an aqueous solution, centrifuged once more, filtered through a 0.2 µm filter, degassed with argon, and stored in an amber vial. As mentioned previously, oxidation may result in the capping compound becoming destabilized; and destabilization can result in irreversible flocculation of the capped quantum dots.

EXAMPLE 2

Figure 1:
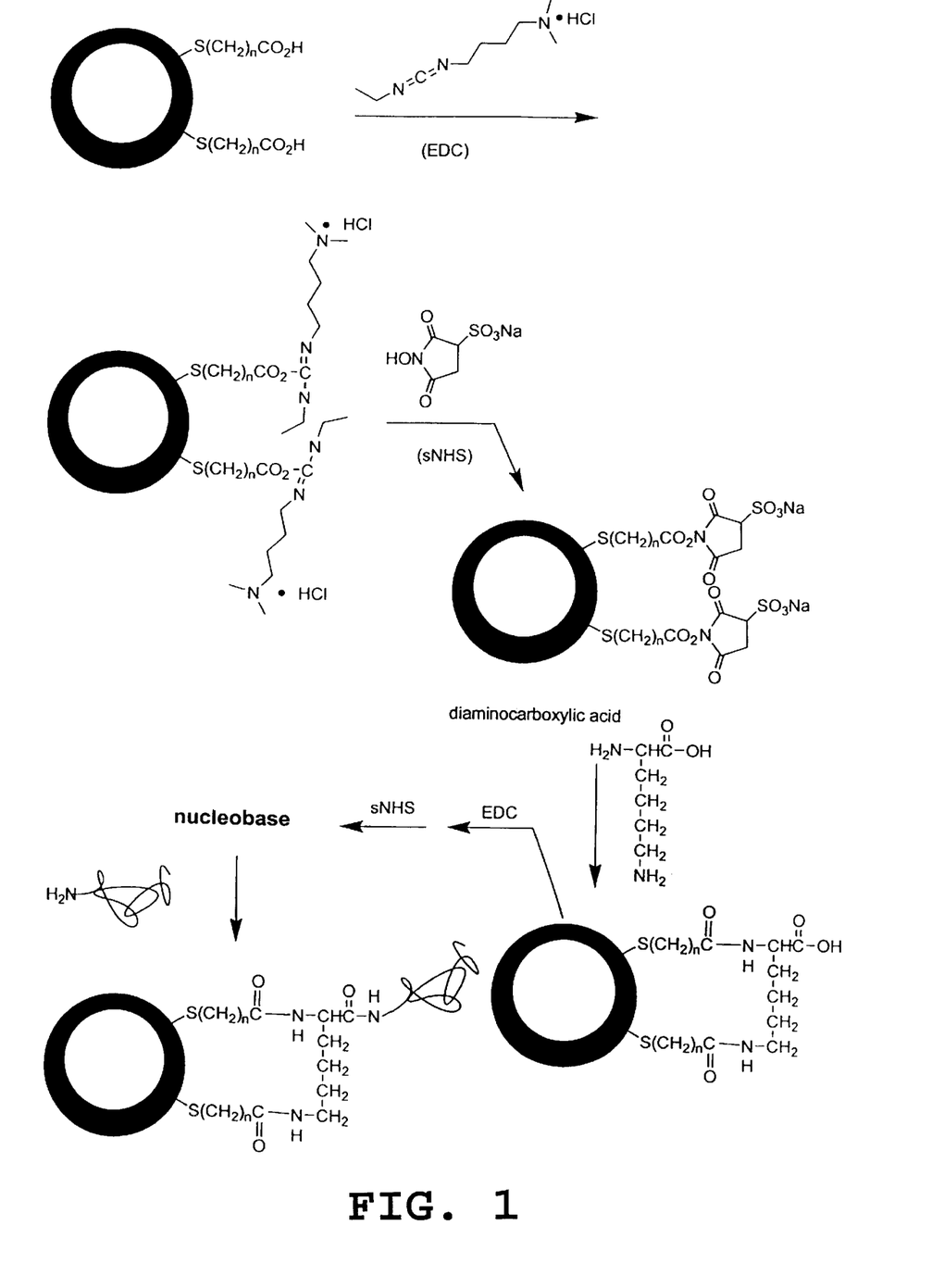
FIG. 1. is a schematic illustrating a functionalized nanocrystal comprising a layer of a capping compound, further comprise a coating of a diaminocarboxylic acid, and then operably linking the diaminocarboxylic acid to a nucleobase.

Illustrated in this Example is a preferred embodiment of exemplary functionalized nanocrystals. Capped CdX core/ YZ shell quantum dots were produced using the methods illustrated in Example 1. The capped quantum dots were functionalized by a the addition of a coating by operably linking organic molecules comprising a diaminocarboxylic acid to the capping compound in forming functionalized nanocrystal. In a preferred embodiment, the diaminocarboxylic acid (a) contributes to the water-solubility of the functionalized nanocrystal because it has polar functional groups which can hydrogen-bond with water; (b) has at least two free functional groups which are carboxyl-reactive, thereby enabling the diaminocarboxylic acid molecule to operably link to, and may crosslink, carboxyl groups extending from the capping compound on the capped quantum dots; (c) once operably linked to the capping compound, has one or more free functional groups which can be used for operably linking to a nucleobase or to a linker which is then operably linked to a nucleobase; and (d) provides other beneficial properties to the resultant functionalized nanocrystals. A preferred diaminocarboxylic acid comprises lysine. For example, and as illustrated in FIG. 1, mercaptoacetic acid-capped quantum dots were dissolved in an aqueous buffer system (pH of about 7). The buffer may comprise such buffers as PBS or HEPES; however, the presence of phosphate may dramatically decrease the lifetime of the cross-linking agent. To the capped quantum dots was added EDC (1-ethyl-3-[3-dimethyl-aminopropyl] carbdiimide) and sulfoNHS (sulfo-N-hydroxysuccinimide) in 500–1000 times excess. The resulting solution was stirred at room temperature for 30 minutes. Mercaptoethanol was added to neutralize unreacted EDC at 20 mM concentration, followed by stirring for 15 minutes. The entire solution was then added dropwise, with stirring, to a solution of lysine (large excess) in the same buffer; and the mixture was stirred for 2 hours at room temperature. Ethanolamine (30 mM) was added to quench the reaction; and the mixture was stirred for 30 minutes at room temperature or left overnight at 4° C. The solution was centrifuged to remove any precipitated solids, and then ultrafiltered through a 30 kD MW centrifugal filter. The resultant concentrated, functionalized nanocrystals can be solubilized in an aqueous solution of choice.

Figure 2A:
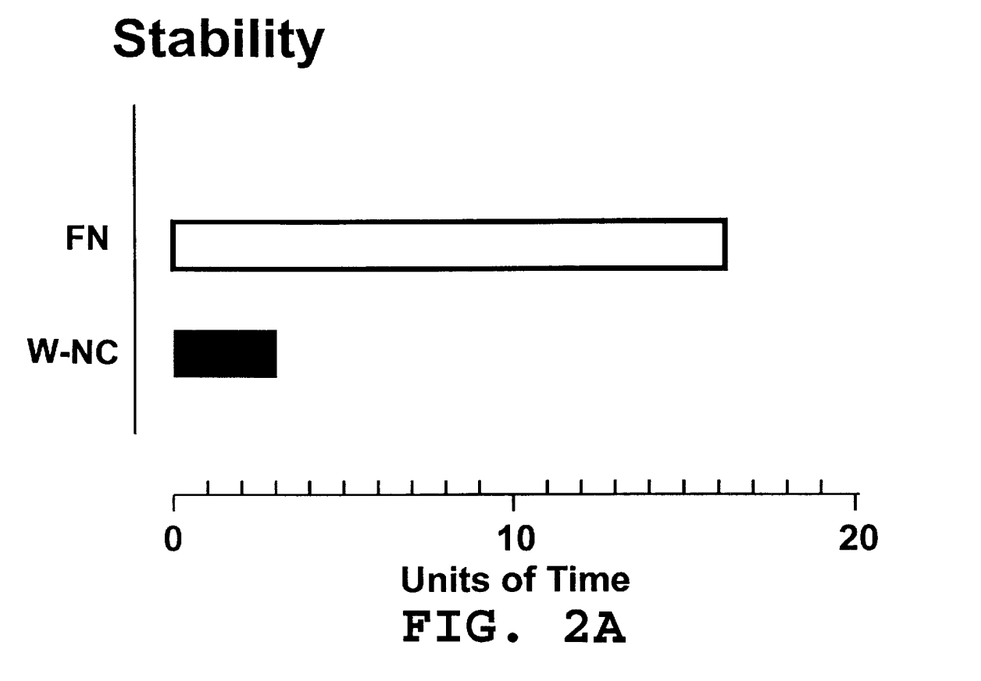
FIG. 2A is a bar graph comparing the stability of capped quantum dots ("W-SN") to the stability of functionalized nanocrystals ("FN") under oxidizing conditions.
Figure 2B:
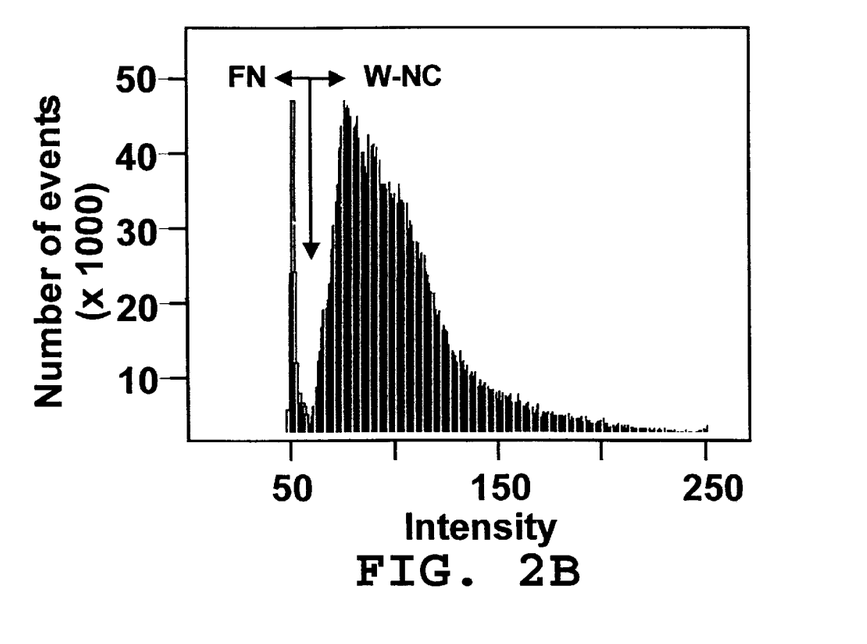
FIG. 2B is a bar graph comparing the non-specific binding of capped quantum dots ("W-SN") to the non-specific binding of functionalized nanocrystals ("FN").

Regarding stability, as shown in FIG. 2A, the functionalized nanocrystals containing a coat of diaminocarboxylic acid ("FN") unexpectedly show a significant increase in stability in an aqueous environment compared to quantum dots having an outer layer of just the capping compound ("W-SN"), when exposed over time to identical conditions of an oxidizing environment (e.g., light and air). Additionally, as shown in FIG. 2B, functionalized nanocrystals containing a coat of diaminocarboxylic acid ("FN") unexpectedly result in a significant decrease in non-specific binding compared to quantum dots having an outer layer of just the capping compound ("W-SN"), when each were contacted with a surface that is both hydrophilic and hydrophobic (e.g., as may be encountered in a detection system), followed by washing of the surface, followed by detection of residual nanocrystals (as measured by number of events of fluorescence versus the intensity of fluorescence; using a fluorescence microscope with a video camera attachment, time of exposure—⅓oth of a second).

In another embodiment, as also illustrated in FIG. 1, the coating comprising diaminocarboxylic acid of a functionalized nanocrystal may then be operably linked to nucleobase; or to a combination comprising a linker which is then operably linked to a nucleobase. For example, depending on factors such as the species of diaminocarboxylic acid and/or the amount of diaminocarboxylic acid which is used to operably link to the capping compound, each operably linked diaminocarboxylic acid may have one or more reactive functionalities (e.g., free amino group, free carboxyl group, and a combination thereof) that can be used to operably link to a reactive functionality of a nucleobase (or to a linker). As an illustrative example, a nucleobase having a free carboxyl-reactive group (e.g., amine group) can be operably linked to a free carboxyl group of a molecule of diaminocarboxylic acid comprising a coating of the functionalized nanocrystals using methods known in the art (e.g., treatment with EDC, followed by treatment with sulfo-NHS, as previously described herein). In an alternative, a nucleobase having a free amino-reactive groups (e.g., a carboxyl group) can be operably linked to a free amino group of a molecule of diaminocarboxylic acid comprising a coating of the functionalized nanocrystals using methods known in the art. If desirable, essentially the same procedure can be used to operably link an additional amino acid layer onto the diaminocarboxylic acid layer, and then to operably link the resultant functionalized nanocrystal to a nucleobase (or linker).

To illustrate this embodiment, molecules representative of nucleobases having free carboxyl-reactive groups (amine groups) were operably linked to the functionalized nanocrystals using the methods summarized herein. Briefly, functionalized nanocrystals (1 ml, $8.1 \times 10^{-9}$ mol) were esterified by treatment with EDC ($8.1 \times 10^{-6}$ mol), followed by treatment with sulfo-NHS ($8.9 \times 10^{-6}$ mol) at ambient temperature in buffered aqueous solution (at about pH 7.4) for 30 minutes. 2-mercaptoethanol was added to the solution at a concentration of 20 mM, and the mixture was stirred for 15 minutes to quench any unreacted EDC. The nanocrystals were then contacted with a mol concentration of molecules (depending on the size, and desired number) for operably linking a plurality of the molecules to the functionalized nanocrystals, and the reaction mixture was stirred for 2 hours (e.g., or reacted in other suitable conditions for forming an amide bond between the EDC-activated carboxylates of the diaminocarboxylic acid molecules and the amine groups of the nucleobases). Ethanolamine was added at a concentration of 30 mM to quench the coupling reaction, and the reaction mixture was stirred for 30 minutes. The resulting solution was then filtered to remove excess reagents. The concentrated material was then diluted to 1 ml in buffer (e.g., PBS) or other suitable aqueous solution.

EXAMPLE 3

Preferably, species of functionalized nanocrystals used to label nucleobases can be excited to emit fluorescence emissions representative of a spectrum of colors. For example, one species of functionalized nanocrystals can emit a spectrally resolvable fluorescence emission peak corresponding to a blue color; another species of functionalized nanocrystals can emit a spectrally resolvable fluorescence emission peak corresponding to a green color; another species of functionalized nanocrystals can emit a spectrally resolvable fluorescence emission peak corresponding to a yellow color; another species of functionalized nanocrystals can emit a spectrally resolvable fluorescence emission peak corresponding to an orange color; and another species of functionalized nanocrystals can emit a spectrally resolvable fluorescence emission peak corresponding to a red color (see, e.g., Table 1). Thus, by exposing the functionalized nanocrystals to an excitation light (visible, or UV, or a combination thereof) that is suitable for exciting the functionalized nanocrystals, the excited functionalized nanocrystals emit characteristic fluorescence peaks that may be detected, and distinguished by spectral resolution. A preferred excitation light is in the spectral range of from about 200 nm to about 500 nm; and more preferably, in the spectral range of from about 300 nm to about 400 nm. In a preferred embodiment, the fluorescence emissions of more than one species of excited functionalized nanocrystals comprises discrete fluorescence peaks in the spectral range of about 400 nm to about 750 nm.

For example, CdSe/ZnS quantum dots having a substantially uniform size comprising a diameter of about 68.4 angstroms (A) may be excited to emit a spectrally resolvable fluorescence peak (orange) at 609 nm which may be detected using appropriate detection means. CdSe/ZnS quantum dots having a substantially uniform size comprising a diameter of about 53.2 A may be excited to emit a spectrally resolvable fluorescence peak (yellow) at 545 nm which may be detected using appropriate detection means. CdSe/ZnS quantum dots having a substantially uniform size comprising a diameter of about 46.6 A may be excited to emit a spectrally resolvable fluorescence peak (green) at 522 nm which may be detected using appropriate detection means. Detection may be by detection means comprising a scanner or reader or other analytical instrument which can detect fluorescence peaks in the range of about 400 nm to about 750 nm; and, optionally (when more than one color is used in the detection system), distinguish between the spectrally resolvable fluorescence peaks within that range. Thus, for example, it will be apparent to those skilled in the art that several species, each species differing in uniform size, of functionalized nanocrystals may be used simultaneously for differentially labeling nucleobases in a process comprising strand synthesis, sequencing a nucleic acid molecule, or a combination thereof. For purposes of illustration, but not limitation, Table 1 illustrates the color represented by fluorescence emission ("Color"), an approximate range of uniform sizes of the core quantum dot for producing each color (in nm, "Size Range"), an approximate range of spectrally resolvable fluorescence emission spectra for the appropriate approximate range of uniform sizes (in nm, "Emission range"), and the range of the ratio of ZnS unit cells per quantum dot ("ZnS Ratio)" when the CdSe quantum dots are passivated with ZnS.

TABLE 1

| Color | Size Range | Emission Range | ZnS Ratio |
| --- | --- | --- | --- |
| blue | 2.5 to 2.68 | 476 to 486 | 310 to 342 |
| green | 2.8 to 3.4 | 500 to 530 | 379 to 498 |
| yellow | 3.58 to 4.26 | 536 to 564 | 530 to 703 |
| orange | 4.9 to 6.1 | 590 to 620 | 882 to 1275 |
| red | 8.6 to 10.2 | 644 to 654 | 2380 to 3263 |

EXAMPLE 4

This example illustrates additional embodiments of labeling (operably linking) a nucleobase to the a functionalized nanocrystal according to the present invention. Additionally, this example illustrates various embodiments of a composition according to the present invention, wherein the composition comprises a functionalized nanocrystal-labeled nucleobase (sometimes also referred to hereinafter as a "labeled nucleobase"). There are several methods by which a nucleobase may be operably linked to the functionalized nanocrystal according to the present invention. Preferably, each nucleobase is operably linked to the functionalized nanocrystal via a reactive functionality, so that the resultant labeled nucleobase can be incorporated into a strand being synthesized using an appropriate polymerase which incorporates nucleobases in a template-directed manner. As discussed in more detail herein, the operably linking of each nucleobase to each functionalized nanocrystal involves use of one or more reactive functionalities comprising an amino group, a thiol group, and amino reactive group, a thiol reactive group, and a combination thereof.

Figure 3:
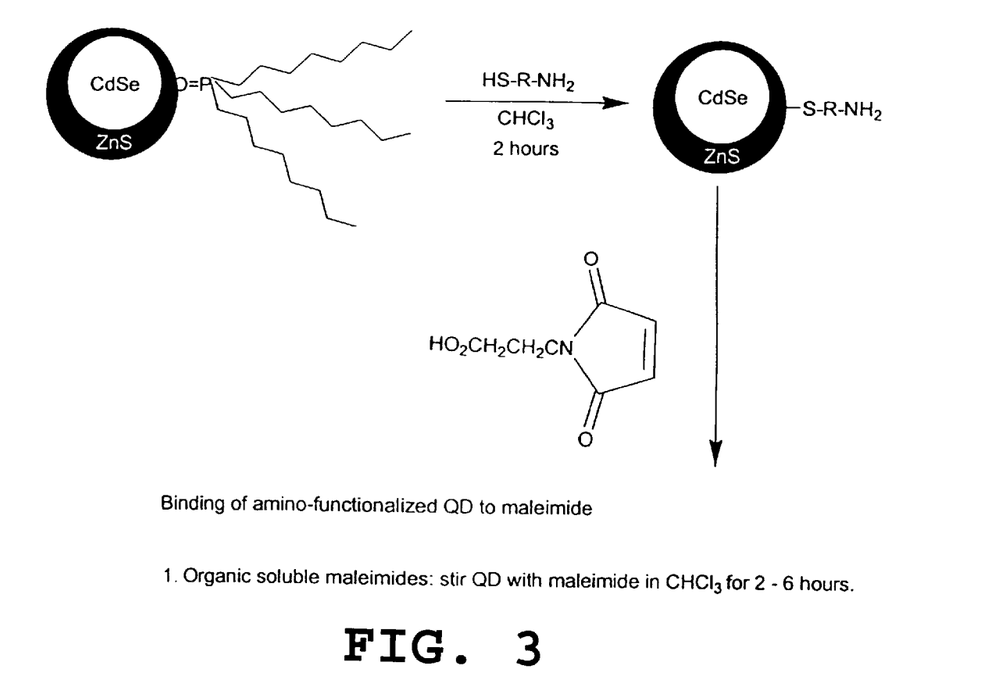
FIG. 3 is a schematic illustration showing a quantum dot being functionalized by a mercaptoamine coating.

In one preferred embodiment, the nucleobase is labeled with (operably linked to) a functionalized nanocrystal according to the present invention by using reactive functionalities comprising thiol group and thiol reactive groups. For example, CdX core/YZ shell quantum dots may capped with mercapto-functionalized amine (e.g., aminoethanethiol-HCl, homocysteine, or 1-amino-2-methyl-2propanethiol-HCl), as illustrated in FIG. 3. These amino group-capped quantum dots are functionalized by the addition (either in the presence or absence of EDC) of a maleimide derivative that reacts with amino groups. Such a maleimide derivative may include, but is not limited to 3-maleimidopropionic acid N-hydroxysuccinimide ester, 3-maleimidopropionic acid, 3-maleimidobenzoic acid N-hydroxysuccinimide ester, 4-(maleimido-methyl)-1-cyclohexanecarboxylic acid N-hydroxysuccinimide ester. The resultant functionalized nanocrystal, having a thiol reactive group, can interact with and bind to a nucleobase previously derivatized with one or more thiol groups. In another preferred example, as shown in FIG. 1, the functionalized nanocrystal may be coated with diaminocarboxylic acid or an amino acid in providing at least one free amine (thiol reactive group). Nucleobases can be derivatized to include thiol groups using methods known to those skilled in the art (see, e.g., U.S. Pat. No. 5,679,785). For example, the OH group located in the 3' and/or 2' position of a nucleobase may be derivatized to a thiol group, thereby allowing interaction with the thiol reactive group of the functionalized nanocrystal, in forming thioether bonds that operably link the nucleobase to the functionalized nanocrystal. In another example, the 3'-O-position and/or the 2'-O-position of a nucleobase may be derivatized to include alkylthiol chemical functionality, which then can be treated with acid under conditions which remove the thiol-protecting group (see, e.g., U.S. Pat. No. 5,578,718). Thus, the nucleobase may be derivatized to include a thiol group, thereby allowing interaction with the thiol reactive group of the functionalized nanocrystal, in forming thioether bonds that operably link the nucleobase to the functionalized nanocrystal.

In another embodiment, the nucleobase is labeled with (operably linked to) a functionalized nanocrystal of the present invention using reactive functionalities comprising amino groups and thiol groups. In this embodiment, a linker is utilized to operably link a functionalized nanocrystal to a nucleobase. For example, and as illustrated in FIG. 3, CdX core/YZ shell quantum dots are capped with mercapto-functionalized amine. In another preferred example, as shown in FIG. 1, the functionalized nanocrystal may be coated with diaminocarboxylic acid or an amino acid in providing at least one free amino group. A nucleobase can be derivatized to include a thiol group using methods known to those skilled in the art. For example, the OH group located in the 3' and/or 2' position of a nucleobase may be derivatized to a thiol group, thereby allowing interaction with a heterobifunctional linker reagent that also reacts with the amino group of the functionalized nanocrystal, in operably linking the nucleobase to the functionalized nanocrystal. Alternatively, the 3'-O-position and/or the 2'-O-position of a nucleobase may be derivatized to include alkylthiol chemical functionality, which then can be treated with acid under conditions which remove the thiol-protecting group. Where one entity (e.g., nucleobase) has a reactive functionality comprising one or more thiol groups, and the other entity has a reactive functionality comprising one or more amino groups (e.g., functionalized nanocrystal), a heterobifunctional linker may be used to bridge the two entities using standard chemical techniques. A hetero-bifunctional linker may include, but is not limited to, sulfo-GMBS, sulfo-MBS, sulfo-SMCC, and sulfo-SMPB (for others, see, e.g., U.S. Pat. No. 5,648,213). As will be apparent to those skilled in the art from the foregoing descriptions, various linker reagents may be used to link a functionalized nanocrystal to a nucleobase according to this embodiment. A preferred linker for DNA sequencing is an alkynylamino group wherein one end of the triple bond is attached to an amine through a substituted or unsubstituted diradical moiety (see, e.g., U.S. Pat. No. 5,151,507). The diradical moiety can comprise a straight chain alkylene, such as $CH_2$, and may further comprise a substitution with a reactive functionality, or may be unsubstituted. When multiple labels are incorporated into the same strand during strand synthesis, the diradical moiety may comprise an unsubstituted chain of from about 10 to about 19 carbon atoms (which may also contain one or more oxygen, nitrogen and sulfur atoms) to provide a linker of sufficient length, flexibility, and hydrophilicity for enzymatic incorporation of the functionalized nanocrystal-labeled nucleobase by a polymerase during strand synthesis.

In another embodiment, the nucleobase is labeled with (operably linked to) functionalized nanocrystals of the present invention using reactive functionalities comprising amino groups. In this embodiment, the functionalized nanocrystal has one or more free amino groups, and the nucleobase is derivatized to include a free amino group, and a linker is used to operably link the nucleobase to the functionalized quantum dot. For example, and as illustrated in FIG. 3, CdX core/YZ shell quantum dots are capped with mercapto-functionalized amine. In another preferred example, as shown in FIG. 1, the functionalized nanocrystal may be coated with diaminocarboxylic acid or an amino acid in providing at least one free amino group. Nucleobases can be derivatized with amino groups using methods known to those skilled in the art. For example, the OH group located in the 3' and/or 2' position of a nucleobase may be derivatized to include an amino group. The amino group of the nucleobase is operably linked to the amino group of the functionalized nanocrystal by use of a homobifunctional reagent. Alternatively, a proparglyethoxyamino nucleoside may be used as a chain-terminating nucleobase, wherein the reactive functionality of this chain-terminating nucleobase comprises the primary amino moiety or the secondary amino moiety. A homobifunctional reagent is used, by employing standard chemical techniques, for operably linking the amino group of the chain-terminating nucleobase to an amino group of the functionalized nanocrystal. Additionally, a silver cation, which binds to 2 amino groups, may be used to operably link the chain-terminating nucleobase to the functionalized nanocrystals via the free amino groups. Homobifunctional cross-linking reagents reactive with free amino groups are known to those skilled in the art to include, but are not limited to, DTSSP, N-hydroxysuccinimide esters, bisimidoesters, alkylamino linkers (see, e.g., U.S. Pat. No. 5,047,519), and the like.

EXAMPLE 5

This example illustrates various embodiments for a method of strand synthesis using the functionalized nanocrystal-labeled nucleobases according to the present invention. Embodiments, other than those that are described herein for purposes of illustration, for using functionalized nanocrystal-labeled nucleobases according to the present invention in a method of strand synthesis will be apparent to those skilled in the art from the descriptions herein. In one embodiment, the strand synthesis comprises incorporating functionalized nanocrystal-labeled chain terminating nucleobases into a modified Sanger-type DNA sequencing protocol. A chain terminating nucleobase refers to a nucleobase which, after incorporation into a strand being synthesized, prevents further strand elongation or strand synthesis or strand extension by a polymerase. Generally, this protocol involves the generation of multiple populations of single-stranded synthesized DNA strands wherein each synthesized strand terminates at a specific nucleotide base by incorporation of an appropriate chain terminating nucleobase. Thus, the populations of synthesized strands will differ in, and therefore be separated by, the size of the synthesized strand as determined by the position of incorporation of a chain terminating nucleobase. Chain terminating nucleobases may include, but are not limited to, dideoxynucleotide triphosphates, dideoxyribonucleoside triphosphates, a proparglyethoxyamino nucleoside, an alkynylaminonucleotide, acyclonucleoside triphosphates, and functional equivalents thereof. In general, detectable levels of the functionalized nanocrystal-chain terminating nucleobases are randomly incorporated as the 3'-terminal nucleotide in strands synthesized using this sequencing protocol. As illustrated in Table 1, the class of fluorescent nanocrystals may comprise a species of functionalized nanocrystal with a spectrally resolvable fluorescence emission peak corresponding to a blue color (for purposes of brevity of description, and not limitation, "blue FN"); a species of functionalized nanocrystal with a spectrally resolvable fluorescence emission peak corresponding to a green color ("green dots"); a species of functionalized nanocrystal with a spectrally resolvable fluorescence emission peak corresponding to a yellow color ("yellow FN"); a species of functionalized nanocrystal with a spectrally resolvable fluorescence emission peak corresponding to a orange color ("orange FN"); and a species of functionalized nanocrystal with a spectrally resolvable fluorescence emission peak corresponding to a red color ("red FN").

In continuing with this example, each different chain terminating nucleobase may be labeled with a species of functionalized nanocrystal capable of emitting fluorescence of a different color. For example, ddATP or a functionally equivalent nucleobase is labeled with a green dot ("green FN-ddATP"), ddCTP or a functionally equivalent nucleobase is labeled with a yellow dot ("yellow FN-ddCTP"), ddGTP or a functionally equivalent nucleobase is labeled with an orange dot ("orange FN-ddGTP"), and ddTTP or a functionally equivalent nucleobase is labeled with a red dot ("red FN-ddTTP"). Various commercial kits may be used for the sequencing reaction using conditions and protocols as recommended by the manufacturer. As will be apparent to one skilled in the art, concentrations of the components will vary depending on such factors relating to the sequencing including, but not limited to, the reaction conditions, the template, the thermostable polymerase, and the nature of the chain terminating nucleobase. In continuing with this illustration, four reactions may be set up and performed simultaneously. Added to each reaction tube in a predetermined amount sufficient for the sequencing reaction is DNA template for sequencing (e.g., 2.5 µg), a primer (e.g., 0.5 pmol), polymerase buffer and $dH_2O$. The template DNA is denatured and the primer is annealed to the template in each reaction tube by incubating each tube in boiling water for two minutes, followed by cooling at room temperature. To each tube is added 5 µl of a nucleotide solution wherein: (a) one tube receives a nucleotide solution comprising appropriate amounts of dATP, dCTP, dGTP, dTTP, and red FN-ddTTP for random incorporation as the 3'-terminal nucleotide in synthesized strands; (b) a second tube receives a nucleotide solution comprising appropriate amounts of dATP, dCTP, dGTP, dTTP, and green FN-ddATP for random incorporation as the 3'-terminal nucleotide in synthesized strands; (c) a third tube receives a nucleotide solution comprising appropriate amounts of dATP, dCTP, dGTP, dTTP, and orange FN-ddGTP for random incorporation as the 3'-terminal nucleotide in synthesized strands; and (d) a fourth tube receives a nucleotide solution comprising appropriate amounts of dATP, dCTP, dGTP, dTTP, and yellow FN-ddCTP for random incorporation as the 31-terminal nucleotide in synthesized strands. Each of the four reactions may then be initiated by the adding the appropriate amount (e.g., 5 units) of a thermostable polymerase, and incubating the tubes at the recommended times and temperatures. Each reaction mixture may then be processed for separating the resultant synthesized strand by size using standard methods known to those skilled in the art. Depending on the type of instrument used to detect and spectrally resolve the fluorescence emission after the strands are exposed to an appropriate light source, the four reactions may be combined together for separation and detection of the respective functionalized nanocrystal-labeled synthesized strands; or each of the four reactions may be separated individually for detection of the respective functionalized nanocrystal-labeled synthesized strands, and the individual separations may be detected simultaneously such as by scanning with subsequent spectral resolution.

In another embodiment, the strand synthesis comprises employing functionalized nanocrystal-labeled nucleobases into a sequencing protocol which relies on primer extension followed by base-specific cleavage of primer extension products. In one example of this embodiment, each nucleobase to be incorporated during strand synthesis is differentially labeled (e.g., with a different species of functionalized nanocrystal), the functionalized nanocrystal-labeled synthesized strand is suspended in a moving fluid flow stream, an exonuclease is used to sequentially cleave an individual functionalized nanocrystal-labeled nucleobase from the end of the suspended synthesized strand, and each cleaved functionalized nanocrystal-labeled nucleobase is maintained in order of cleavage for subsequent detection, spectral resolution, and identification using an appropriate detection system (see, e.g., U.S. Pat. No. 4,962,037). As will be apparent to one skilled in the art, another variation of this embodiment involves operably linking a functionalized nanocrystal according to the present invention to the nucleobase after it is cleaved (post-replication, post-cleavage). Various commercial kits may be used for the sequencing reaction using conditions and protocols as recommended by the manufacturer. Each different nucleobase may be labeled with a different species of functionalized nanocrystal, wherein each species has a spectrally resolvable fluorescence emission corresponding to a different color (e.g., different than the other species used). For example, dATP or a functionally equivalent nucleobase is labeled with a green FN ("green FN-dATP"), dCTP or a functionally equivalent nucleobase is labeled with a yellow FN ("yellow FN-dCTP"), dGTP or a functionally equivalent nucleobase is labeled with an orange FN ("orange FN-dGTP"), and dTTP or a functionally equivalent nucleobase is labeled with a red FN ("red FN-dTTP"). After strand synthesis, the resultant synthesized strand is suspended in a flowing sample stream containing an effective amount of exonuclease which sequentially cleaves a nucleobase from the free end of the immobilized synthesized strand. Each cleaved nucleobase is then carried by the stream, passed through a single light source for exciting the functionalized nanocrystal operably linked to the cleaved nucleobase, and then passed through a detector wherein the functionalized nanocrystal-labeled cleaved nucleobase is detected and identified by the spectrally resolvable fluorescence emission wavelength characteristic of the species of functionalized nanocrystal that is operably linked to the cleaved nucleobase; thereby allowing the determination of the sequence of the synthesized strand by the identity and position of each nucleobase comprising the synthesized strand.

As presented in the examples previously described herein, either a synthesized strand being analyzed for the presence and position of a functionalized nanocrystal-labeled nucleobase, or a functionalized nanocrystal-labeled nucleobase cleaved therefrom, may be analyzed for the detection and identification of the nucleobase by exposing the functionalized nanocrystal-labeled nucleobase to an excitation light source, detecting and spectrally resolving the emitted fluorescence peak, relating the fluorescence peak with a species of functionalized nanocrystal (e.g., see Table 1), and relating the species of functionalized nano-crystal to the specific type of nucleobase for which it was used to label; thereby identifying the nucleobase labeled and its position (present or former) in the synthesized strand. Appropriate detection means (e.g., light source, scanner, one or more photodetectors, filters, photomultipliers, processing software, and the like) which can be utilized to detect and spectrally resolve different fluorescence peaks emitted by the functionalized nanocrystals of the present invention (such as when they are operably linked to nucleobases), are known to those skilled in the art (see, e.g., U.S. Pat. Nos. 4,962,037, 5,430,541, 5,436,130, and 5,543,026). Depending on the nature of the strand synthesis, such detection means may include, but are not limited to, single molecule tracking systems, array scanners, synchronous fluorescence detection systems, and other systems capable of detecting, spectrally resolving, and processing fluorescence emissions. In general, the detection means may comprise a scanner or reader or other analytical instrument which can detect discrete fluorescence peaks that fall in a spectral range of about 400 nm to about 750 nm; and, optionally (when more than one color is used in the detection system), distinguish between spectrally resolvable fluorescence peaks within that range. The ratio of the intensities (quantum yield) of the spectrally resolvable fluorescence emissions of the species of functionalized nanocrystals used to differentially label nucleobases may then be used to determine the identity of the labeled nucleobase and/or the sequence of the synthesized strand from which it is derived. Generally, the functionalized nanocrystal-labeled nucleobase, or a strand incorporating the same, can be separated in space, and/or time, and/or size, so as to be detected, and then be spectrally resolved by the detection means. In a preferred embodiment, the detection system comprises an excitation light source capable of efficiently exciting a set of multiple species of functionalized nanocrystals used to differentially label the nucleobases sought to be detected; and comprises detection means for detecting and spectrally resolving the discrete fluorescence emission spectra that can be emitted by the excited functionalized nanocrystals.

Also embodied in the present invention is a kit for use in a process selected from the group consisting of strand synthesis, sequencing a synthesized strand, or a combination thereof. In one embodiment the kit comprises a functionalized nanocrystal-labeled nucleobase. In another embodiment, the kit may further comprises additional species of functionalized nanocrystal-labeled nucleobases, each species being separately packaged. Thus, in this preferred embodiment, the kit comprises a plurality of species of functionalized nanocrystal-labeled nucleobases, with each species being separately packaged (e.g., in separate containers). For example, in a preferred embodiment, the kit may comprise a set of four solutions of functionalized nanocrystal-labeled nucleobases, wherein each solution comprises an amount of a functionalized nanocrystal-labeled nucleobase comprising a nucleobase type that is different than that present in any other solutions of the set, and wherein each nucleobase type is differentially labeled with a species of functionalized nanocrystal (e.g., the fluorescence emission of the functionalized nanocrystals present in one solution is spectrally resolvable as compared to the fluorescence emission of functionalized nanocrystals of any other solutions in the set). In one preferred variation of this embodiment, the set of four solutions comprise: in a first container, an amount of a functionalized nanocrystal-labeled nucleobase wherein the nucleobase is dATP or a functionally equivalent nucleobase; in a second container, an amount of a functionalized nanocrystal-labeled nucleobase wherein the nucleobase is dCTP or a functionally equivalent nucleobase; in a third container, and amount of a functionalized nanocrystal-labeled nucleobase wherein the nucleobase is dGTP or a functionally equivalent nucleobase; and in a fourth container, a functionalized nanocrystal-labeled nucleobase wherein the nucleobase is dTTP or a functionally equivalent nucleobase. In another variation of this embodiment, the set of four solutions comprise, in separate containers, an amount of a functionalized nanocrystal-labeled nucleobase wherein the nucleobase is ddATP or a functionally equivalent chain terminating nucleobase; an amount of a functionalized nanocrystal-labeled nucleobase wherein the nucleobase is ddCTP or a functionally equivalent chain terminating nucleobase; an amount of a functionalized nanocrystal-labeled nucleobase wherein the nucleobase is ddGTP or a functionally equivalent chain terminating nucleobase; and an amount of a functionalized nanocrystal-labeled nucleobase, wherein the nucleobase is ddTTP or a functionally equivalent chain terminating nucleobase. In another preferred embodiment, the kit comprises a plurality of the separately packaged functionalized nanocrystal-labeled nucleobases, wherein such nucleobases are selected from the group consisting of deoxynucleotides, chain-terminating nucleobases, and a combination thereof.

In another embodiment, the kit according to the present invention comprises, in separate packaging: an amount of a functionalized nanocrystal having one or more reactive functionalities; and an amount of a nucleobase having one or more reactive functionalities. In a preferred embodiment, the one more reactive functionalities is selected from the group consisting of an amino group, a thiol group, an amino reactive group, a thiol reactive group, a carboxyl-reactive group, a carboxyl group, and a combination thereof. The kit may further comprise an amount of a linker which can be used to operably link the functionalized nanocrystal to the nucleobase.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed is:

1. A functionalized nanocrystal-labeled nucleobase comprising a functionalized nanocrystal operably linked to a nucleobase; wherein the functionalized nanocrystal comprises a core and a shell, a capping compound comprising a compound having the formula $HS(CH_2)_nX$ wherein X is a carboxylate, and a coating comprising diaminocarboxylic acid which is operably linked to the capping compound; and wherein the diaminocarboxylic acid of the functionalized nanocrystal comprises one or more reactive functionalities, and the nucleobase comprises one or more reactive functionalities, which are used to operably link the functionalized nanocrystal to the nucleobase.

2. The functionalized nanocrystal-labeled nucleobase according to claim 1, further comprising a linker which operably links the functionalized nanocrystal to the nucleobase.

3. The functionalized nanocrystal-labeled nucleobase according to claim 1, wherein the one more reactive functionalities is selected from the group consisting of an amino group, a thiol group, an amino reactive group, a thiol reactive group, a carboxyl-reactive group, a carboxyl group, and a combination thereof.

4. The functionalized nanocrystal-labeled nucleobase according to claim 1, wherein the least one additional coating comprises an amino acid, and wherein the amino acid comprises diaminocarboxylic acid.

5. The functionalized nanocrystal-labeled nucleobase according to claim 1, wherein the amino acid comprises diaminocarboxylic acid.

6. A kit for using functionalized nanocrystal-labeled nucleobases in a process selected from the group consisting of strand synthesis, sequencing a synthesized strand, and a combination thereof, the kit comprising a plurality of species of functionalized nanocrystal-labeled nucleobases, wherein an amount of each species of functionalized nanocrystal-labeled nucleobase is separately packaged, wherein each species of functionalized nanocrystal-labeled nucleobase comprises a different nucleobase type than the nucleobase type of the other species of the plurality of species of functionalized nanocrystal-labeled nucleobases, and wherein each species of functionalized nanocrystal-labeled nucleobase is differentially labeled with a species of functionalized nanocrystal that can emit a fluorescence emission that is spectrally resolvable as compared to the species of functionalized nanocrystals used to label the other species of the plurality of species of functionalized nanocrystal-labeled nucleobases.

7. The kit according to claim 6, wherein the nucleobase type include in the kit is selected from the group consisting of deoxynucleotides, chain-terminating nucleobases, and a combination thereof.

8. A kit comprising, in separate packaging: an amount of a functionalized nanocrystal having one or more reactive functionalities; and an amount of a nucleobase having one or more reactive functionalities; wherein the functionalized nanocrystal comprises a core and a shell, a capping compound comprising a compound having the formula $HS(CH_2)_nX$ wherein X is a carboxylate, and a coating comprising diaminocarboxylic acid which is operably linked to the capping compound.

9. The kit according to claim 8, wherein the one more reactive functionalities is selected from the group consisting of an amino group, a thiol group, an amino reactive group, a thiol reactive group, a carboxyl-reactive group, a carboxyl group, and a combination thereof.

10. The kit according to claim 8, further comprising a linker which can be used to operably link the functionalized nanocrystal to the nucleobase.

11. A functionalized nanocrystal-labeled nucleobase comprising a functionalized nanocrystal operably linked to a nucleobase; wherein the functionalized nanocrystal comprises a core and a shell, a capping compound comprising a compound having the formula $HS(CH_2)_nX$ wherein X is a carboxylate, and at least one additional coating comprising an amino acid which is operably linked to the capping compound; and wherein a coating of the at least one additional coating comprises one or more reactive functionalities, and the nucleobase comprises one or more reactive functionalities, which are used to operably link the functionalized nanocrystal to the nucleobase.

12. The functionalized nanocrystal-labeled nucleobase according to claim 11, further comprising a linker which operably links the functionalized nanocrystal to the nucleobase.

13. The functionalized nanocrystal-labeled nucleobase according to claim 11, wherein the one more reactive functionalities is selected from the group consisting of an amino group, a thiol group, an amino reactive group, a thiol reactive group, a carboxyl-reactive group, a carboxyl group, and a combination thereof.

14. A functionalized nanocrystal-labeled nucleobase comprising a functionalized nanocrystal operably linked to a nucleobase; wherein the functionalized nanocrystal comprises a core and a shell, a capping compound comprising homocysteine, and at least one additional coating selected from the group consisting of a maleimide derivative, and an amino acid; and wherein a coating of the at least one additional coating comprises one or more reactive functionalities, and the nucleobase comprises one or more reactive functionalities, which are used to operably link the functionalized nanocrystal to the nucleobase.

15. The functionalized nanocrystal-labeled nucleobase according to claim 14, further comprising a linker which operably links the functionalized nanocrystal to the nucleobase.

16. The functionalized nanocrystal-labeled nucleobase according to claim 14, wherein the one more reactive functionalities is selected from the group consisting of an amino group, a thiol group, an amino reactive group, a thiol reactive group, a carboxyl-reactive group, a carboxyl group, and a combination thereof.

17. A kit comprising, in separate packaging: an amount of a functionalized nanocrystal having one or more reactive functionalities; and an amount of a nucleobase having one or more reactive functionalities; wherein the functionalized nanocrystal comprises a core and a shell, a capping compound comprising a compound having the formula $HS(CH_2)_nX$ wherein X is a carboxylate, and at least one additional coating comprising an amino acid which is operably linked to the capping compound.

18. The kit according to claim 17, wherein the one more reactive functionalities is selected from the group consisting of an amino group, a thiol group, an amino reactive group, a thiol reactive group, a carboxyl-reactive group, a carboxyl group, and a combination thereof.

19. The kit according to claim 17, further comprising a linker which can be used to operably link the functionalized nanocrystal to the nucleobase.

20. A kit comprising, in separate packaging: an amount of a functionalized nanocrystal having one or more reactive functionalities; and an amount of a nucleobase having one or more reactive functionalities; wherein the functionalized nanocrystal comprises a core and a shell, a capping compound comprising homocysteine, and at least one additional coating selected from the group consisting of a maleimide derivative, and an amino acid.

21. The kit according to claim 20, wherein the one more reactive functionalities is selected from the group consisting of an amino group, a thiol group, an amino reactive group, a thiol reactive group, a carboxyl-reactive group, a carboxyl group, and a combination thereof.

22. The kit according to claim 20, further comprising a linker which can be used to operably link the functionalized nanocrystal to the nucleobase.

\* \* \* \* \*

UNITED STATES PATENT AND TRADEMARK OFFICE
CERTIFICATE OF CORRECTION

PATENT NO. : 6,221,602 B1  
DATED : April 24, 2001  
INVENTOR(S) : Barbera-Guillem, Nelson, & Castro Page 1 of 1

It is certified that error appears in the above-identified patent and that said Letters Patent is hereby corrected as shown below:

Renumber claims 6-10 as claims 4-8.
Renumber claims 11-13 as claims 9-11.
Renumber claim 5, to be claim 12, so as to be dependent on newly numbered claim 9 as follows.
12. The functionalized nanocrystal-labeled nucleobase according to claim 9, wherein the amino acid comprises diaminocarboxylic acid.

Renumber claim 14 as claim 13.
Renumber claim 4, to be claim 14, so as to be dependent on newly numbered claim 13 as follows.
14. The functionalized nanocrystal-labeled nucleobase according to claim 13, wherein at least one additional coating comprises an amino acid, and wherein the amino acid comprises diaminocarboxylic acid.

Signed and Sealed this

Eighth Day of January, 2002

*Attest:*

JAMES E. ROGAN  
*Attesting Officer*   *Director of the United States Patent and Trademark Office*